United States Patent [19]
Yoneda et al.

[11] Patent Number: 4,779,199
[45] Date of Patent: Oct. 18, 1988

[54] PATIENT MONITOR

[75] Inventors: Kiwamu Yoneda; Kazuhiro Kuwa, both of Osaka, Japan

[73] Assignee: Sumitomo Electric Industries, Ltd., Osaka, Japan

[21] Appl. No.: 904,371

[22] Filed: Sep. 8, 1986

Related U.S. Application Data

[63] Continuation-in-part of Ser. No. 755,771, Jul. 15, 1985, abandoned.

[30] Foreign Application Priority Data

Jul. 13, 1984 [JP] Japan ................................. 59-146376

[51] Int. Cl.⁴ .......................... G06F 15/42; A61B 5/04
[52] U.S. Cl. .................. 364/413.03; 364/550; 364/413.02; 364/413.06; 364/413.09; 128/630; 128/710
[58] Field of Search ............... 364/551, 554, 555, 413, 364/415–417; 128/630, 632, 706, 709, 710

[56] References Cited

U.S. PATENT DOCUMENTS

| | | | |
|---|---|---|---|
| 4,250,888 | 2/1981 | Grosskopf | 128/706 |
| 4,417,306 | 11/1983 | Citron et al. | 128/703 |
| 4,513,295 | 4/1985 | Jones et al. | 364/415 |

Primary Examiner—Parshotam S. Lall
Assistant Examiner—Brian M. Mattson
Attorney, Agent, or Firm—Cushman, Darby & Cushman

[57] ABSTRACT

A patient monitor monitors information on body condition. The monitor includes a sensor for detecting information on body condition and converting the detected information into an electrical analog signal. The electrical analog signal is converted into digital measured values and sampled by a data processor at a predetermined time interval. Or, the data processor calculates a representative data value from a predetermined number of digital measured values to obtain summary data. Continuity or discontinuity is determined from successive blocks of summary data. A read-write storage for the summary data and two different kinds of delimiters correspond to the cases where the continuity and discontinuity of successive blocks of summary data are identified. The data processor operates to read out and process the stored summary data as a block of summary data covering the oldest date to the first discontinuity delimiter or a block from one discontinuity delimiter to the succeeding discontinuity delimiter and to edit the summary date into a histogram for every block of the summary data.

5 Claims, 8 Drawing Sheets

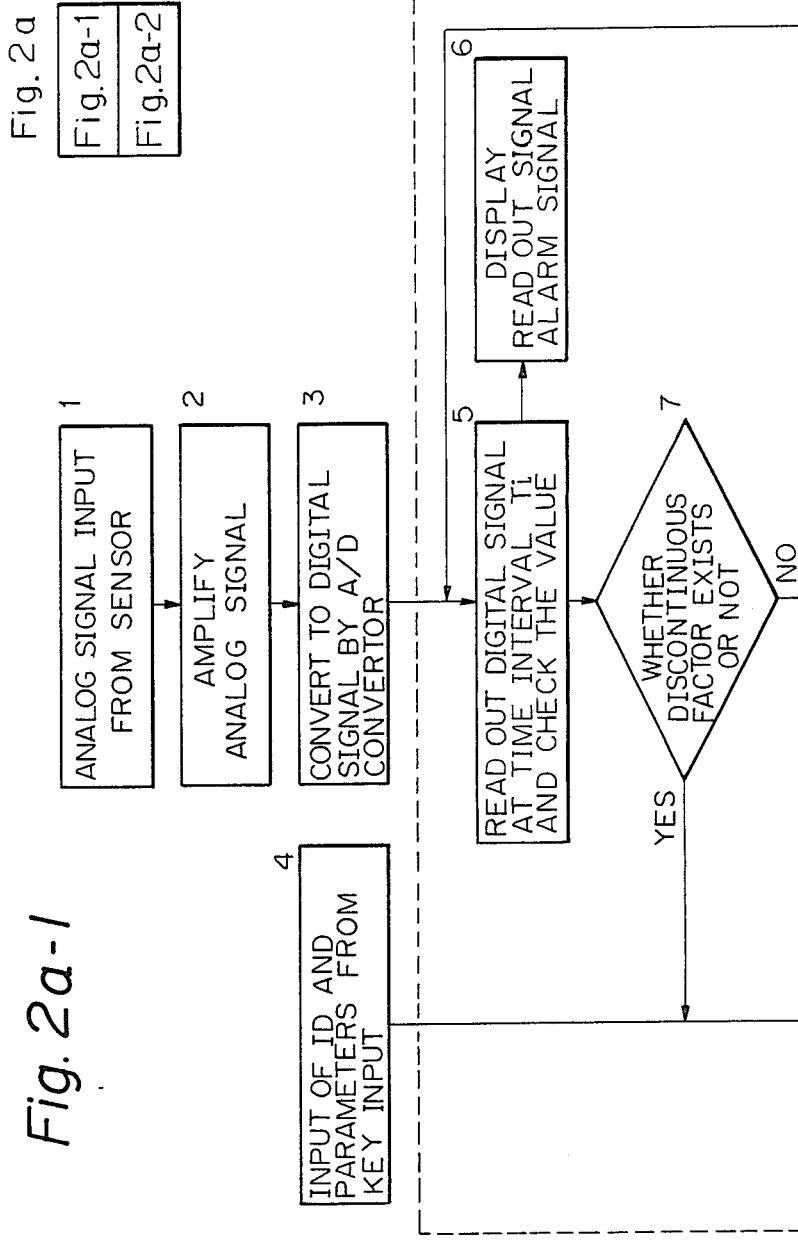

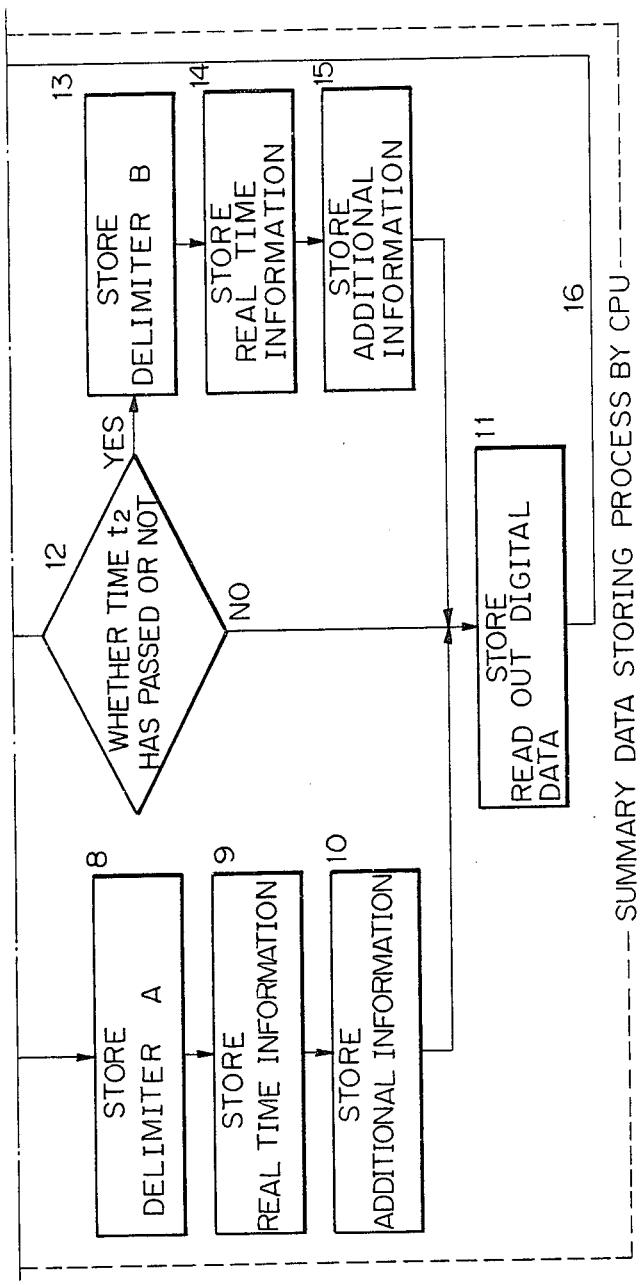

PATIENT MONITOR

This is a continuation-in-part application of U.S. patent application Ser. No. 755,771 filed on July 15, 1985, now abandoned.

BACKGROUND OF THE INVENTION

1. Field of the Art

This invention relates to medical appliances and, more particularly, to patient monitors capable of converting information on the state of a living body from human patients such as electrocardiogram, heart rate or blood $PO_2$/oxygen tension into electrical signals, storing the electrical signals, processing the electrical signals if necessary, editing the electrical signals and outputting them as summary data.

2. Prior Art

Prior art devices for measuring information on the condition of patients which are being observed by continuous monitoring of such functions as electrocardiogram, blood pressure or the like are designed to instantly output the measured values of such information and record the measured values on a recording paper or display them on a CRT (Cathode Ray Tube). A physician then examines the recorded or displayed values to monitor the condition of the patient.

The known method for instantly outputting measured data of such information and recording or displaying the measured data has, for example, the drawbacks enumerated hereinbelow and physicians have desired that the drawbacks inherent in this method be eliminated. The drawbacks are:

(a) The volume of paper on which the information is recorded becomes increasingly large as the measuring time elapses.

(b) Since data in wave form extends as a long line on the CRT or recording paper, it is difficult to pinpoint extraordinary or special points when seeking to diagnose a patient.

(c) Storage of the information records is not easy.

The present invention has as its aim the provision of a patient monitor capable of effectively eliminating the drawbacks inherent in conventional patient monitors and of editing information on the condition of a body in proper form and reducing it to summary data.

Another object of the present invention is to provide a patient monitor capable of displaying or recording such information in edited form.

A further object of the present invention is to provide a patient monitor which is portable and serves as a data collection terminal unit.

SUMMARY OF THE INVENTION

The patient monitor according to the present invention is designed to detect information on the condition of a body from a patient's body by means of a sensor, convert the detected information into an electrical analog signal, and convert the electrical analog signal into digitized measured value data at a predetermined timing which depends upon the type of information being monitored. A plurality of representative data values are taken out of the measured value data and these representative data values are stored in storing means as summary data.

The continuity or discontinuity of successive blocks of summary data each of which is constituted by a predetermined number of items of the summary data is determined by a data processing means and two different kinds of delimiters which respectively correspond to the cases where continuity and discontinuity are identified by the data processing means stored in the storing means prior to storing of the summary data.

A real time signal is given by a real time clock and is stored in the storage area of the storing means following the delimiter but preceding the summary data.

The stored summary data are processed as a block of data covering the oldest data to the first discontinuity delimiter or a block from one discontinuity delimiter to the succeeding discontinuity delimiter and are edited into a histogram for every block of summary data. These edited data are output in accordance with an output command or instruction.

Furthermore, the patient monitor of the present invention may incorporate therein means for displaying or recording (printing) the output of the edited data. Further, if necessary, the means for displaying or recording the edited data may be an external displaying or recording means which is connected to the patient monitor by means of a cable.

Additionally, the patient monitor of the present invention may be designed as a portable device by incorporating a battery power source therein whereby the monitor can function as a data terminal unit for collection of information on the condition of a body.

By using the discontinuity delimiter, discontinuity in the summary data can be detected. If only the discontinuity delimiter is adopted, however, when summary data covering a long period are continuously stored in a limited storage area of the storing means and the storage area in which the discontinuity delimiter is stored is overwritten, the real time information and other index data information succeeding the discontinuity delimiter are erased by overwriting and, therefore, the continuous summary data following these items of information become useless. To avoid these problems, the continuity delimiter is stored at every block of summary data in this invention, as stated above, and this prevents the continuous summary data being rendered useless.

The above and other objects and attendant advantages of the present invention will be more readily apparent to those skilled in the art from a reading of the following detailed description in conjunction with the accompanying drawings which show one preferred embodiment of the invention for illustrative purposes only and which do not limit the scope of the same in any way.

BRIEF DESCRIPTION OF THE DRAWINGS

FIGS. 2a-1 and 2a-2, which together form FIG. 2a, are diagrams showing a data processing program for storing summary data and other information in the patient monitor according to the invention;

PREFERRED EMBODIMENTS OF THE INVENTION

Figure 1:
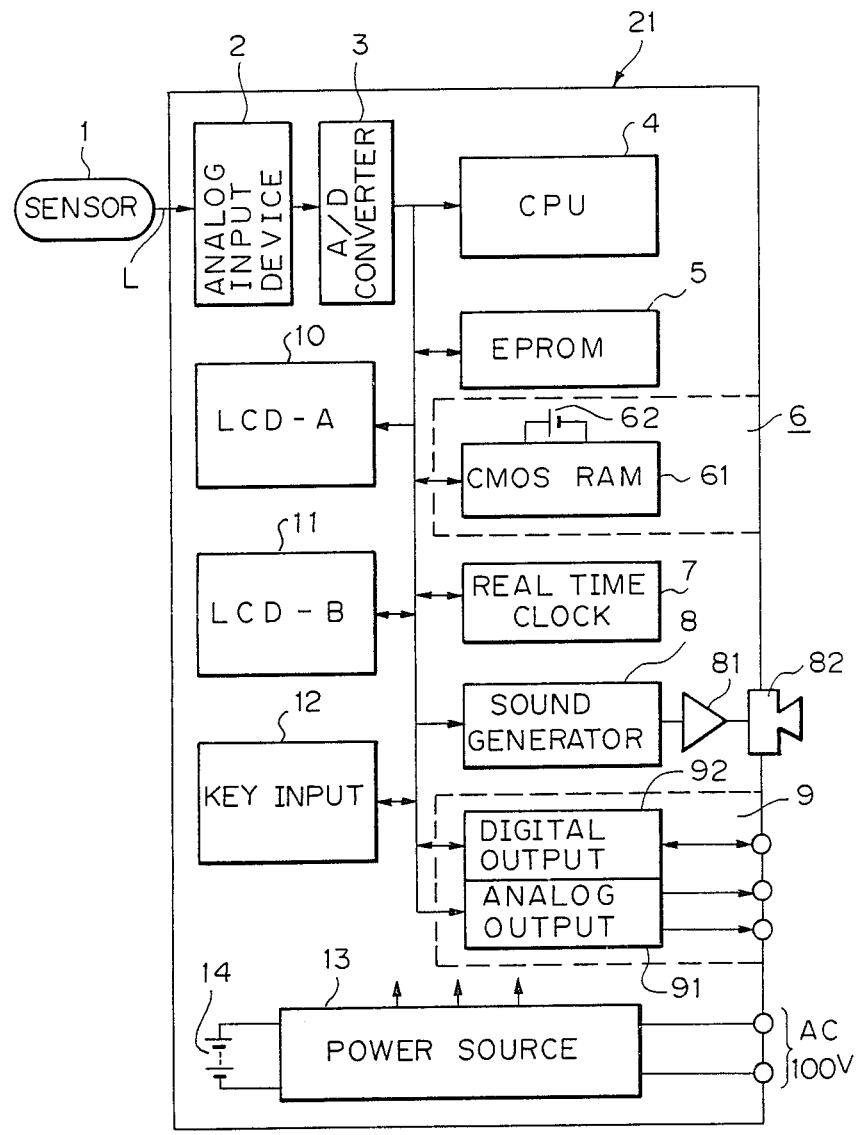
FIG. 1 is a diagram of the system of the principal components constituting the patient monitor according to the present invention.

One preferred embodiment of the patient monitor according to the present invention will now be described. FIG. 1 is a diagram of the system of the principal components of the patient monitor embodying the present invention. The system of FIG. 1 will be explained hereinbelow referring to the diagrams of FIGS. 2a and 2b which respectively show data processing for storing summary data and outputting edited summary data by CPU 4. In FIG. 1, a sensor 1 attached to a patient (not shown) detects an item of information such as blood $PO_2$/oxygen tension, and the detected information is fed as an electrical analog signal through a lead L to an analog input device 2 (Step 1). The analog input device 2 amplifies the analog signal and feeds the amplified analog signal to an A/D (analog/digital) converter 3 (Step 2). The A/D converter 3 converts the electrical analog signal into an electrical digital signal each time the converter receives a sampling signal from a CPU 4 and feeds the electrical digital signal to the CPU 4 (Step 3). An EPROM (erasable and programmable ROM) 5 stores a program for controlling the entire system shown in FIG. 1. A memory 6 consists of a CMOS RAM 61 and a lithium cell 62 for making the RAM 61 up. The RAM 61 is provided with an area where summary data transferred from the CPU 4 and ID (Index Data) information including day and time relating to the summary data and stored, and an area where parameters input thereto from a key input 12 and adapted to convert the data form of the digital signal into body condition information data are stored. This ID information and the parameters are input in advance from the key input 12 (Step 4). The RAM 61 and CPU 4 reciprocate data therebetween. A real time clock circuit 7 outputs real time information relating to day, hour, minute and second and a timing signal to the CPU 4. The CPU 4 outputs a sampling signal at a predetermined time interval Ti based on a timing signal transmitted from the real time clock circuit 7 and obtains an electrical digital signal at the relevant time interval from the A/D converter 3 (Step 5). Furthermore, the CPU 4 reads parameters corresponding to monitored information on body condition out of the RAM 61 and converts the data form of the digital signal into measured value data in accordance with these parameters. A representative value is selected as "summary data" from the converted data (measured value data).

The selection of the above-mentioned summary data may be performed by extracting measured value data as summary data at a time interval n×Ti or extracting measured value data at a time interval Ti and then averaging n measured value data to obtain single summary data. The time interval Ti, number of measured value data n and data extraction procedures referred to above are selectively and suitably employed in dependence upon the type of body condition data to be monitored. For example, for monitoring blood $PO_2$/oxygen tension, summary data are extracted at a time internal of n×Ti=20 sec. under the conditions of Ti=1.0 sec. and n=20. In this case, when one data is expressed by 16 bits, in order to store summary data corresponding to 8-consecutive hours measurement, a capacity capable of storing an area over about 3K bytes is sufficient.

The CPU 4 feeds the measured value data in succession to a measured value display (LCD-A) 10 which displays the same data (Step 6). The measured value display 10 is formed of liquid crystal and has a display capacity of 7 segments×4. Furthermore, the CPU 4 transfers summary data obtained from measured value data in a predetermined number to the RAM 61 which stores the summary data together with other data like time data representing the time of extraction of the summary data as will be explained hereinafter.

When the summary data is stored in the RAM 61, the CPU 4 determines the continuity or discontinuity successive items of summary data (Step 7). Namely, when the power source is turned on or turned off or when monitoring is shifted from one patient to another one and readjustment of the sensor is effected, these factors cause discontinuity in the summary data. When such discontinuity in the summary data is identified by the CPU 4, a delimiter A which shows discontinuity in the summary data is stored in the storage area of the RAM 61 (Step 8), and then real time information relating to day, hour, minute and second is read out from the real time clock 7 and stored in the storage area of the RAM 61 (Step 9). Further, additional necessary ID information such as input channel, dynamic range of the recorder, sampling time interval, etc. is stored in the storage area (Step 10). Thereafter, read out digital data is stored in the storage area of the RAM 61 (Step 11).

On the other hand, when the CPU 4 confirms the continuity of the summary data in Step 7, i.e. when there are no factors such as to cause discontinuity in the data, a delimiter B which shows or represents the continuity of the data is stored in the storage area of the RAM 61 after elapse of a predetermined time interval $t_2$ (Steps 12, 13). Thereafter, as is similar to the case in which discontinuity of the data is identified, real time information and additional ID information are stored (Steps 14, 15) and, then, the digital data read out is stored in the storage area of the RAM 61 (Step 11). After the digital data read out is stored in the RAM 61, the process returns to Step 5 for further reading out of digital data (Step 16).

In Step 12, if the predetermined time interval $t_2$ is not exceeded, the process directly advances to Step 11. This means that delimiter B and the succeeding real time and additional ID information are stored periodically after storing of a predetermined number of summary data.

When the obtained value data measured exhibit critical values, the CPU 4 identifies such values and outputs an alarm signal to a sound generator 8 which in turn outputs an alarm through an amplifier 81 to an alarm speaker 82 which produces an acoustic alarm (Steps 5 and 6). Simultaneously, the CPU 4 can transfer a danger message from the EPROM 5 to a message display (LCD-B) 11 which displays the danger message. The message display 11 is formed of liquid crystal and has a display capacity of 16 letters×2 lines to serve as an auxiliary unit of the display 10.

The key input 12 has the function of presetting the above-mentioned parameters in the RAM 61 as well as an additional function of instructing the RAM 61 to output summary data stored therein. A power source 13 is supplied with power at AC 100 V from an external power supply and rectifies AC voltage to DC voltage for charging a cell 14. The power source 13 also supplies necessary power to the components constituting the system. The cell 14 serves as the battery power source. It is to be noted that the system shown in FIG. 1 is so constructed as to be portable and can be effectively used as a data collection terminal unit.

Figure 3A:
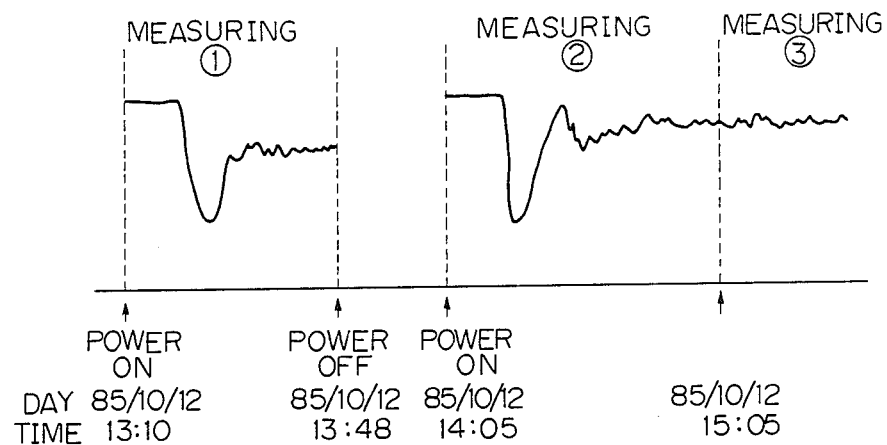
FIG. 3a is a view showing one example of summary data being measured.

FIG. 3a shows one example of a process of measuring percutaneous oxygen partial pressure (tcPO$_2$) of a patient. In this measuring process, the power source is turned on for the commencement of measuring on 85/10/12 (day) at 13:10 (time) and the power source is turned off when measuring is stopped on 85/10/12 at 13:48. Thereafter, the power source is turned on to start measuring again on 85/10/12 at 14:05 and the measuring is continued for more than one hour.

Figure 3B:
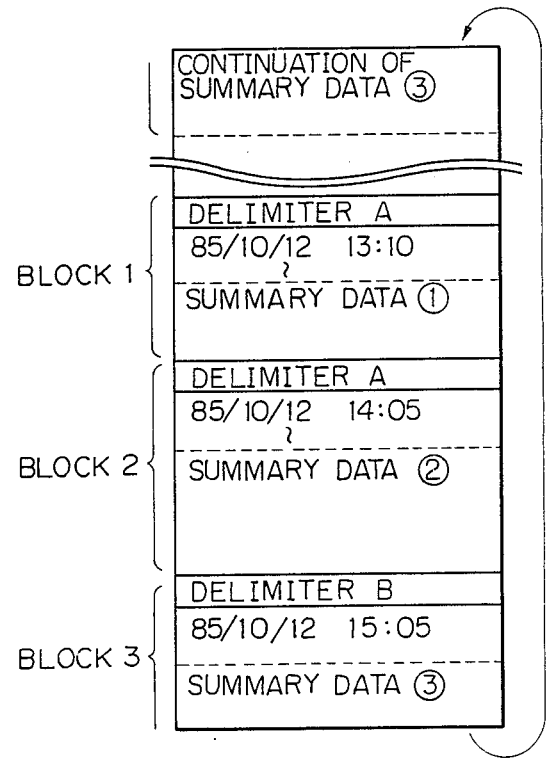
FIG. 3b is a diagram of the storage areas of the RAM wherein the summary data shown in FIG. 3a and other information are to be stored.

FIG. 3b shows the manner in which the data of this measuring process is stored in the storage area of the RAM 61.

In block 1 of the storage area, the summary data ① corresponding to the measurement ① from 85/10/12, 13:10 to 85/10/12, 13:48 shown in FIG. 3a is stored. At the beginning of this block 1, delimiter A which shows the discontinuity of the data is stored and the day and time 85/10/12, 13:10 at which the first summary data occurred and other information are stored following the delimiter A. Likewise, in block 2 of the storage area, the summary data ② corresponding to the measurement ② from 85/10/12, 14:05 to 85/10/12, 15:05 shown in FIG. 3a is stored and delimiter A which shows the discontinuity of the data and the day and time 85/10/12, 14:05 at which the first summary data occurred and other information are stored at the beginning of the block 2. In block 3 of the storage area, the summary data ③ corresponding to the measurement ③ starting at 85/10/12, 15:05 shown in FIG. 3a is stored. In this case, since the summary data ③ is continuous with the summary data ② and predetermined time interval $t_2$ has passed, delimiter B which shows the continuity of the data is stored at the beginning of the block 3. Also, the day and time 85/10/12, 15:05 at which the first summary data occurred and other information are stored following the delimiter B. During the course of storing the summary data ③, since the storing process has by now reached the end of the storage area, the succeeding storage of the summary data returns to the beginning of the storage area of the RAM 6. In this way, the summary data corresponding to measurement of the most recent block of time representing several hours can always be stored. In this method, however, since the storage area is used cyclically, when the ID information relating to the delimiter A or B, day, time, etc. is erased by overwriting, the day and time on which the first summary data occurred or other index data of an associated block of summary data is made unclear. To avoid such problems, the delimiter B and ID information including real time information are inserted at each predetermined time interval $t_2$ in this invention, even if measuring is continued for a long time. Thus the danger of losing all the index data of an associated block of summary data is prevented.

Figure 2B:
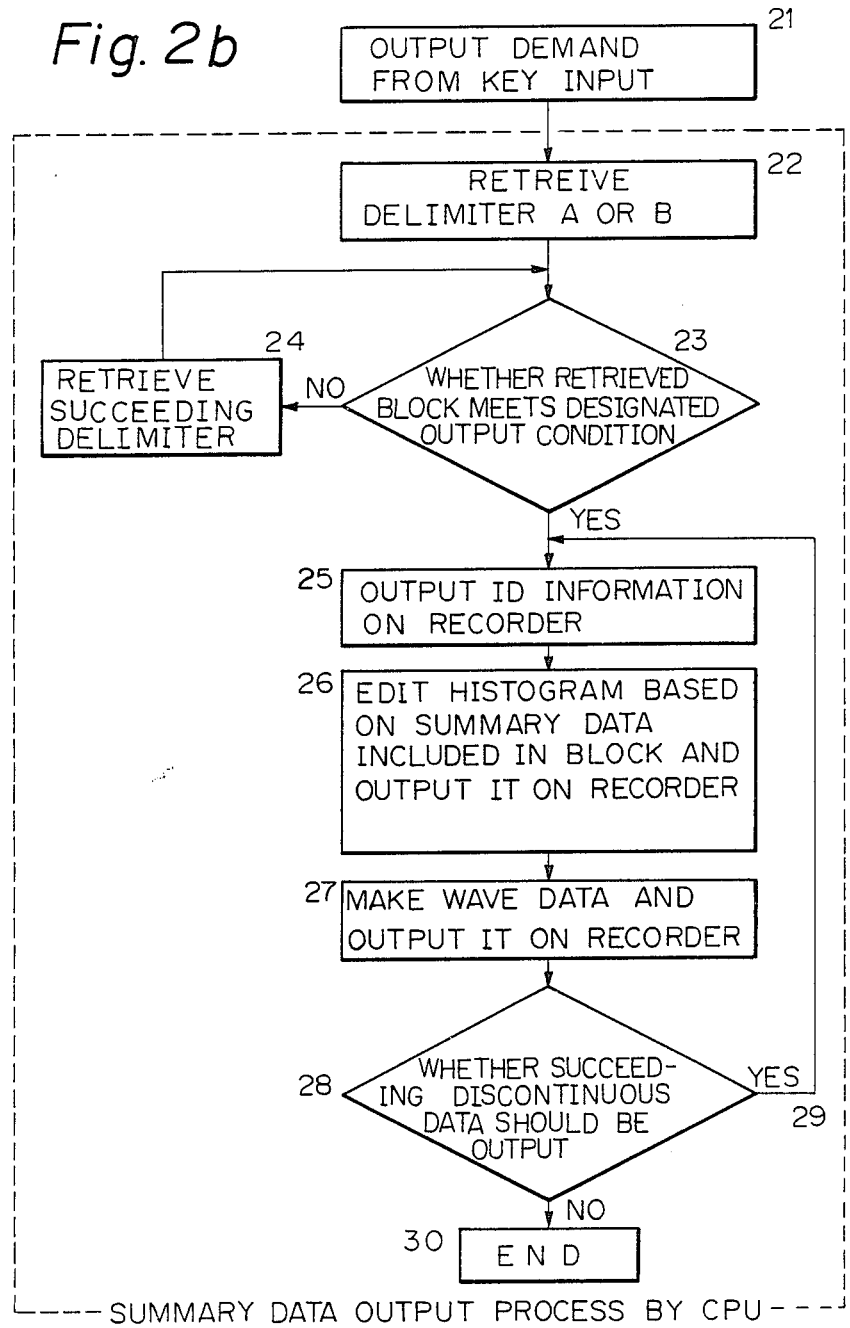
FIG. 2b is a diagram showing a data processing program for outputting edited summary data and other information from the patient monitor according to the invention.

Next, the process for outputting edited summary data is explained referring to FIG. 2b.

At the outset, an output demanding signal is given by inputting the appropriate output conditions through the key input 12 (Step 21). Examples of such conditions are (a) to output all stored data from the oldest data to the most recent data, (b) to output data covering the oldest data to the m-th item of discontinuous data or (c) to output data covering the past n-th data to the most recent data.

When such output demanding signal is given, the CPU 4 firstly retrieves the delimiter A or B to thereby detect designated summary data stored in the storage area of the RAM 61 (Step 22). When the delimiter A or B is found, the CPU 4 reads out ID information including day, time, etc. stored in the storage area following the delimiter and determines whether or not the retrieved block of summary data meets the designated output condition (Step 23). If not, the CPU 4 retrieves the succeeding delimiter A or B (Step 24). If yes, the CPU 4 converts the output form of the ID information such as day, time, etc. in order to adapt the output thereof to a predetermined communication procedure and outputs them to the digital output 92 of the output region 9 at a predetermined timing determined by the CPU 4 (Step 25). Thereafter, the CPU 4 edits summary data included in this block and succeeding block(s) which is(are) positioned ahead of the next delimiter A showing discontinuity of the data in a form (in this case a histogram) which can easily be read by the person monitoring it, for example, a physician, converts the output form thereof so as to adapt them to a predetermined communication procedure, and outputs them to the digital output 92 (Step 26). Further, the CPU 4 changes the summary data used for editing the histogram to an output form of a wave form data and outputs them to the digital output 92 (Step 27). After the completion of outputting these summary data, the CPU 4 reads out ID information such as day, time, etc. included in the following discontinuous block of summary data, and compares this ID information with the output condition given in Step 21 to determine whether or not this ID information meets the output condition (Step 28). If yes, the process returns to Step 25 and a similar data output process to that stated above is repeated (Step 29). If no, the data output process is completed (Step 30). The digital output 92 is a data transmission system of international standard and consists of a digital interface RS-232C. The output region 9 also has an analog output 91 which is adapted to be connected to a pen recorder or the like which requires an analog signal input. That is, when the analog output 91 is provided with measured value data or summary data from the CPU 4, the analog output 91 converts the data from digital into analog and outputs them as an analog signal.

Figure 4:
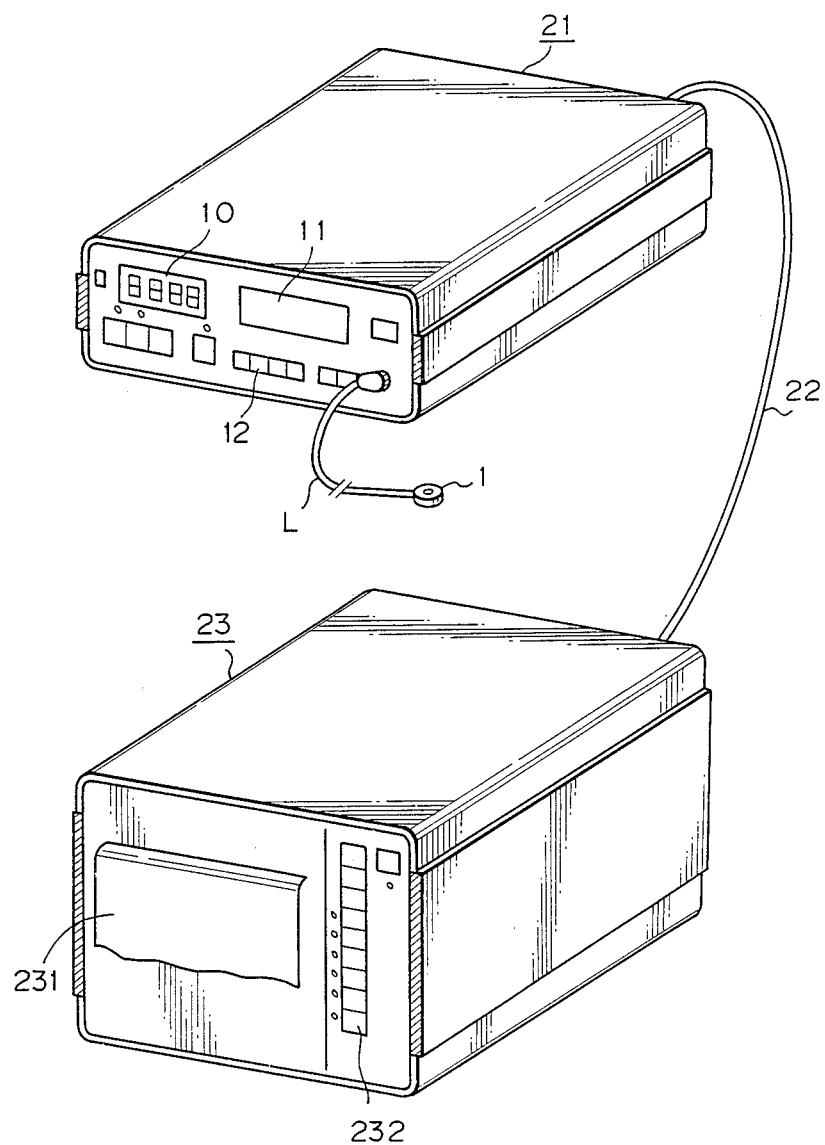
FIG. 4 is a perspective view of the patient monitor employed together with an external recorder.

FIG. 4 is a perspective view of the patient monitor embodying the present invention in which the main body 21 encircled by the solid line, the sensor 1, lead L, measurement display 10, message display 11 and key input 12 are indicated with numbers which correspond to those shown in FIG. 1. The output terminal of the digital output 92 shown in FIG. 1 is connected to a summary output exclusive recorder 23 by means of a cable 22. In FIG. 4, reference numeral 231 denotes a graphic printer and reference numeral 232 denotes a key input.

Figure 5:
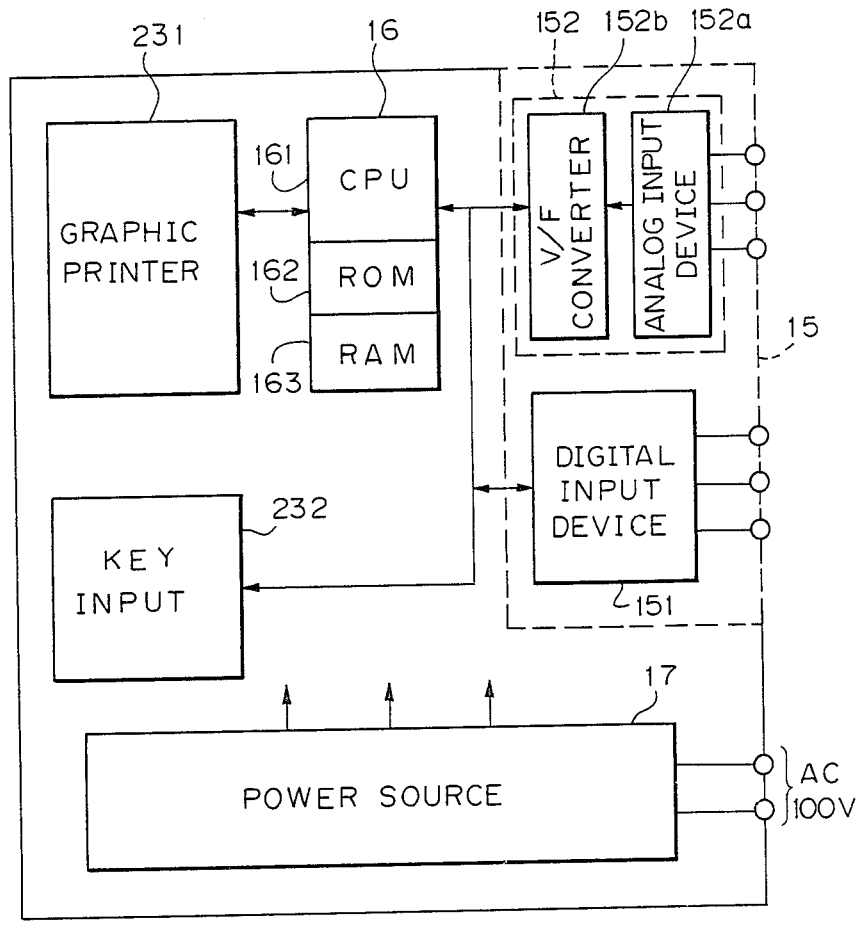
FIG. 5 is a diagram of the system of the components of the external recorder as shown in FIG. 4.

FIG. 5 shows a diagram of the system of the principal components of the recorder 23 and the cable 22 is connected to the input terminal of a digital input 151 of the input region 15. The digital input 151 consists of a digital interface RS-232C. Summary data input to the digital input 151 are fed to a control 16. The input region 15 is provided with an analog interface 152 for processing an analog input. The analog interface 152 consists of an analog input 152a and a V/F (voltage/frequency) converter 152b and analog data input to the input 151 are converted into digital data which are fed to the control 16.

The control 16 consists of a CPU 161, a ROM 162 and a RAM 163. Summary data fed to the control 16 are processed in accordance with the instructions from the key input 232 in the CPU 161 and output to the graphic printer 231. The graphic printer 231 employs a stepping motor whereby printing and paper feed are performed in predetermined amounts at predetermined time intervals in accordance with control signals from the CPU 161. Assuming that printing is performed by one step per summary data, the printer can be controlled quite simply. In such a case, when summary data taken from the sampling time of 20 seconds are output to a graphic printer having a 1/6 mm printing step, data produced during a period of 1 hour can be recorded on a chart 30 mm in length. The graphic printer 231 is preferably a thermal graphic printer because such printers perform printing very quietly. The components of the recorder 23 are supplied with a necessary amount of power from the power source 17 with rectifies AC 100 V.

Figure 6:
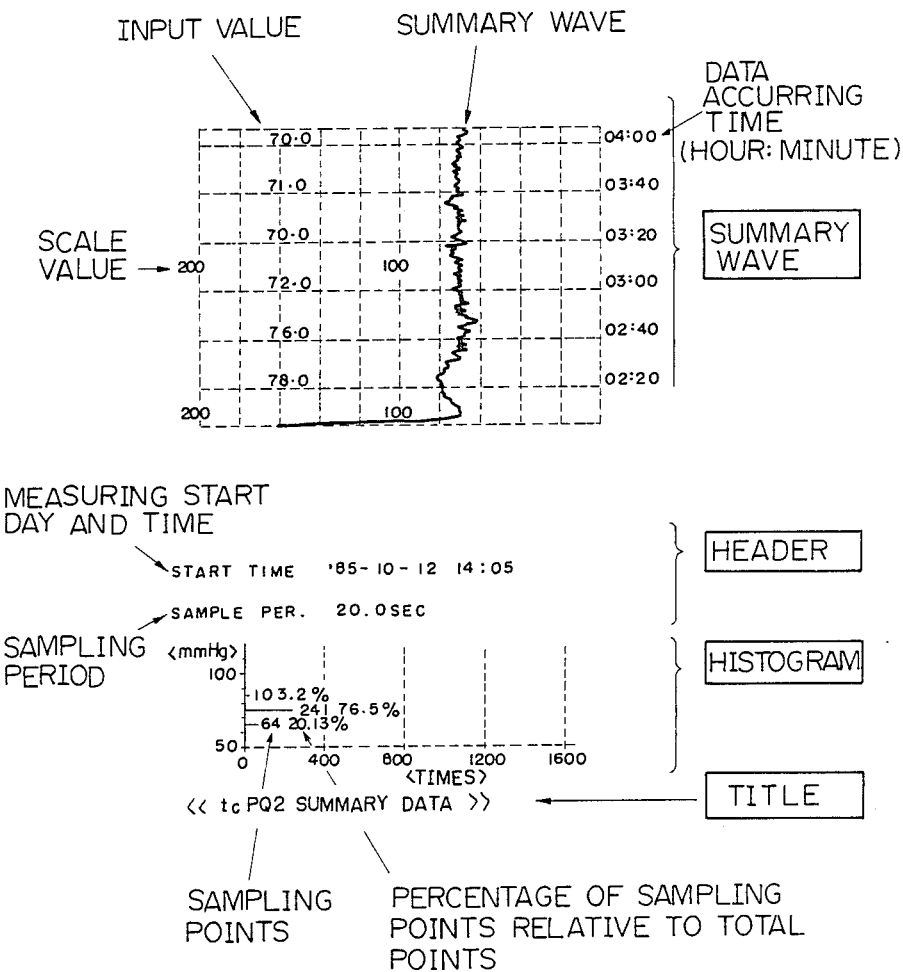
FIG. 6 is a view showing one example of summary data, ID (Index Data) information, histogram and other information printed out by means of the external recorder shown in FIG. 5.

FIG. 6 shows an example of output of the ID information and the summary data ② and ③ stored in the blocks 2 and 3 shown in FIGS. 3a and 3b. Since these summary data ② and ③ are continuous, they are processed as continuous data. The "Histogram" shown is formed by classifying the summary data at a predetermined regular interval (in this case 10 mmHg), counting the number of data belonging to each class and calculating a percentage representing the number in each class relative to the total number of data. The histogram is edited by processing the summary data in every continuous block of summary data. For example, if there are m-summary data $N_1, N_2, N_3, \ldots N_m$ in a single continuous series of summary data and these summary data are to be classified at intervals represented by a predetermined value $\Delta N$, the number of data belonging to each class is counted by solving the following equation (1).

$$N + i \cdot \Delta N \leq N_k < N + (i+1) \cdot \Delta N \quad (1)$$

Where N: initial value
i = 0, 1, 2, 3, ... n
k = 1, 2, 3, 4, ... m

By solving this equation, if the number of data belonging to each class was defined as $n_0, n_1, n_2, \ldots n_i, \ldots n_n$, the percentage representing the number in each class relative to the total number of the data could be calculated by the following equation (2).

$$\frac{n_i}{m} \times 100 \, (\%) \quad (2)$$

From this histogram, the distribution and the average value of the measured values can easily be estimated. "Header" includes ID information such as days, times, etc. which are stored at the beginning of the block 2. From this, it is possible to obtain information such as time at which the summary data being output were first occurred. "Summary wave" is a restored copy of the measurements ② and ③ given by successively outputting the summary data ② and ③.

When the patient monitor embodying the present invention is employed, since data are extracted from information on body condition which is produced successively and are stored and output, various items of such information can be compared with each other and examined, and data occurring over a long period of monitoring can be edited and extracted. Furthermore, it is also possible where necessary to pick out only the important portions from a series of recorded data and then to examine these fully. Additionally, savings in the amount of recording paper used can be attained and storage of the paper is made very easy.

In the illustrated embodiment, although the patient monitor is a separate type in which the monitor main body 21 is connected to the recorder 23 by means of the cable 22, it is also contemplated by the present inventors that the monitor main body 21 of FIG. 1 and the recorder 23 of FIG. 3 may be housed in a common case.

While we have shown and described a specific embodiment of the invention, it will be understood that the same is described merely for the purpose of illustration and that various other forms may be devised within the scope of the invention as defined in the appended claims.

What is claimed is:

1. A patient monitor for monitoring information on body condition comprising:
    a sensor for detecting information on body condition and converting the detected information into an electrical analog signal;
    means operatively coupled to said sensor for converting said electrical analog signal into digital measured values;
    a data processing means operatively coupled to said means for converting for at least one of sampling said digital measured values at a predetermined time interval and calculating a representative data value from a predetermined number of said digital measured values to obtain a summary data, and determining at least one of a continuity and a discontinuity of successive summary data obtained;
    a read-write storing means operatively coupled to said data processing means for storing said summary data and first and second types of delimiters which respectively show a continuity and a discontinuity of summary data determined by said data processing means, whereby said summary data is stored with a respective type delimiter in a storage area of said storing means, said storing means having a back-up function for holding data stored therein and being adapted to be overwritten upon being filled with data;
    a real time clock operatively coupled to said data processing means for outputting real time information for storage in said storage area of said storing means following storing of said respective type of delimiter;
    said data processing means operating to read out and process said stored summary data as at least one of a block of summary data covering an oldest data to a first discontinuity delimiter and a block from a first discontinuity delimiter to a second discontinuity delimiter and to edit said summary data into a histogram for every block of said summary data; and
    means operatively coupled to said data processing means for outputting said edited data in accordance with an outputting instruction.

2. The patient monitor as set forth in claim 1, in which said data processing means seeks an average of said measured values.

3. The patient monitor as set forth in claim 1, further including means for recording or displaying said edited data from said output means.

4. The patient monitor as set forth in claim 3, in which said means for recording or displaying said data is connected to said output means by a cable.

5. A patient monitor as set forth in claim 1, further including a battery power source so as to be portable.

* * * * *